United States Patent [19]

Komatsu et al.

[11] 4,214,100
[45] Jul. 22, 1980

[54] PROCESS FOR PREVENTING BLACKENING OF PHTHALIC ACID

[75] Inventors: Makoto Komatsu; Tazuo Ohta; Toru Tanaka; Kimiko Akagi, all of Kurashiki, Japan

[73] Assignee: Mitsubishi Gas Chemical Company, Inc., Tokyo, Japan

[21] Appl. No.: 857,709

[22] Filed: Dec. 5, 1977

Related U.S. Application Data

[63] Continuation of Ser. No. 657,279, Feb. 11, 1976, abandoned.

[30] Foreign Application Priority Data

Feb. 18, 1975 [JP] Japan ................................. 50-20090

[51] Int. Cl.$^2$ ............................................. C07C 51/33
[52] U.S. Cl. ........................................................ 562/416
[58] Field of Search .................. 260/524 R, 523 A; 562/416

[56] References Cited

U.S. PATENT DOCUMENTS

| | | | |
|---|---|---|---|
| 2,963,509 | 12/1960 | Barker et al. | 260/524 |
| 3,334,135 | 8/1967 | Ichikawa | 260/524 |
| 3,595,908 | 7/1971 | Lumbroso et al. | 260/524 |
| 3,846,487 | 11/1974 | Shigeyasu et al. | 260/524 |

OTHER PUBLICATIONS

Olah, "Friedel–Crafts & Related Reactions", vol. 1, (1963), p. 116.

*Primary Examiner*—A. Siegel
*Attorney, Agent, or Firm*—Armstrong, Nikaido, Marmelstein & Kubovcik

[57] ABSTRACT

In the production of phthalic acid by oxidizing, in a liquid phase, tolualdehyde with molecular oxygen or a gas containing the molecular oxygen in the presence of heavy metal salt containing a Mn salt, especially both Mn and Co salts, and a bromine compound, using a lower aliphatic monocarboxylic acid as a reaction solvent, a blackening of phthalic acid is effectively prevented by conducting the oxidation of tolualdehyde in the presence of an alkylbenzene in an amount satisfying the following formula (1);

$$M \leq -0.15A^2 + 15A + 40 \qquad (1)$$

wherein M is a Mn atom concentration in ppm by weight on the basis of the reaction solution, and A is an amount in % by weight of the alkylbenzene added on the basis of the total of tolualdehyde and said alkylbenzene, and is in a range of from more than 0 to 50 inclusive.

11 Claims, No Drawings

PROCESS FOR PREVENTING BLACKENING OF PHTHALIC ACID

This is a continuation, of application Ser. No. 657,279, filed Feb. 11, 1976 now abandoned.

This invention relates to a process for producing phthalic acid by oxidizing corresponding tolualdehyde with molecular oxygen or a gas containing molecular oxygen in the presence of heavy metal salt containing a Mn salt, especially both Mn and Co salts, and a bromine compound using a lower aliphatic monocarboxylic acid as a solvent.

Japanese Patent Publication No. 2666/59 discloses a process for producing an aromatic carboxylic acid by oxidizing, in a liquid phase, the corresponding aromatic compound having at least one aliphatic substituent with molecular oxygen or a gas containing molecular oxygen in the presence of heavy metal salt containing a Mn salt, and a bromine compound as a catalyst, using a lower aliphatic monocarboxylic acid as a solvent, and production of terephthalic acid from p-xylene, production of isophthalic acid from m-xylene, etc., based on said process are carried out in a large scale.

According to said Japanese Patent Publication No. 2666/59, a Mn salt is an excellent catalyst, and also a Co salt is an excellent catalyst for the oxidation reaction of aromatic hydrocarbons.

Journal of the Chemical Society of Japan (Industrial Chemistry Section) 70 1155 (1967) discloses that, in the production of terephthalic acid by oxidizing p-xylene with molecular oxygen in the presence of a bromine compound and heavy metal salt as the catalyst, using acetic acid as a solvent, Co is the best as the catalyst component, and Mn is the second-best. It is well known that the combination of Mn and Co brings about a considerable synergistic effect (for example, S. Kamiya: Yuki Sanka Hanno (Organic Oxidation Reaction), page 259 (1974), published by Gihodo Publishing Co.).

Japanese Patent Publication No. 36732/70 discloses a process for producing highly purified terephthalic acid suitable for direct polymerization only by oxidation of p-xylene, without any special purification procedure, utilizing the effective catalytic action of the Co salt and especially said synergistic effect of the combination of Co and Mn. That is, it is seen from the prior knowledges so far available that, in producing terephthalic acid by oxidizing p-xylene with molecular oxygen or a gas containing the molecular oxygen in the presence of a bromine compound and heavy metal salts using a lower aliphatic monocarboxylic acid such as acetic acid, etc. as a solvent, it is most effective to use the combination of Co salt and Mn salt.

Furthermore, Journal of the Chemical Society of Japan (Industrial Chemistry Section) 67 1396 (1964) discloses in detail that, in the oxidation of p-xylene to terephthalic acid in a system containing a Mn salt as a catalyst component, p-xylene is successively oxidized to p-tolualdehyde, then to p-toluic acid, and then to 4-carboxybenzaldehyde (4-CBA) in this order. Therefore, it seems at the first glance that terephthalic acid of high purity could be readily obtained by oxidizing p-tolualdehyde, in place of p-xylene, using said well known catalyst system in the same way as the prior art. However, according to oxidation reaction tests conducted by the present inventors using p-tolualdehyde as a raw material in place of p-xylene under the conventional oxidation reaction conditions of p-xylene, blackened terephthalic acid is surprisingly formed. Such a phenomenon has not been experienced in the oxidation of p-xylene, and it was found that the blackening results from contamination of the product terephthalic acid with Mn used as the catalyst. Furthermore, it was found that polyesters of high whiteness cannot be obtained from the resulting blackened terephthalic acid by reacting it with glycols, and that the black colour of the terephthalic acid is not readily removed by the well known purification procedures, such as washing with acetic acid, etc., or recrystallization from acetic acid or water, or purification according to the special recrystallization procedure disclosed in Japanese Pat. Publication No. 16860/66, and that polyesters of high whiteness cannot be obtained by the reaction of the thus treated terephthalic acid with glycols. That is, it was found that only industrially insignificant terephthalic acid is obtained from p-tolualdehyde by the application of the same oxidation technique as applied to p-xylene as a raw material.

Heretofore, terephthalic acid has been produced from p-xylene as a raw material in a large scale continuous process, which obviously owes to the development of art such as the inventions disclosed in Japanese Pat. Publications No. 2666/59, 36732/70, etc. p-Xylene as a raw material for terephthalic acid is prepared through complicated process, such as isomerization, crystallization, or fractional distillation of the mixed xylenes. On the other hand, it is known that p-tolualdehyde is readily synthesized from toluene and carbon monoxide, but its industrial scale production process has not yet been established. However, owing to the recent development and practice of isomerization-separation technique of xylenes using hydrogen fluoride and boron trifluoride as a catalyst, the industrial scale production of p-tolualdehyde from toluene and carbon monoxide has been made possible (Japanese Pat. Publication No. 29760/64).

As toluene can be much more readily produced, and purified in an industrial scale than p-xylene, p-tolualdehyde is now regarded as a very important raw material for terephthalic acid. However, when p-tolualdehyde is used as a raw material for terephthalic acid, it is impossible to produce industrially significant terephthalic acid by mere application of the prior technique of producing terephthalic acid from p-xylene, as described above.

As a result of researches to develop a process for synthesizing industrially significant terephthalic acid by oxidizing tolualdehyde with molecular oxygen or a gas containing the molecular oxygen in the presence of a bromine compound and heavy metal salt containing a Mn salt as the catalyst using a lower aliphatic monocarboxylic acid as a solvent, the present inventors had already succeeded in producing phthalic acid of high whiteness by maintaining the Mn salt concentration at 40 ppm. or less on the basis of Mn metal in the reaction solution when tolualdehyde is oxidized (Japanese Pat. application No. 19312/75). The reaction solution means a total of solvent and water.

As a result of further researches, the present inventors have found that a limit of Mn salt concentration that causes no blackening contamination of phthalic acid by the Mn compound can be extended by adding an alkylbenzene to tolualdehyde in the oxidation process of tolualdehyde with molecular oxygen or a gas containing the molecular oxygen in the presence of a catalyst containing Mn salt, that is, by oxidizing tolualdehyde in a mixture with the alkylbenzene, and have established the present invention.

Advantages of extending available range of the Mn salt concentration are an assurance of industrially stable operation and an increase in phthalic acid yield at the same time. It has been also found unexpectedly that the elevation of the limit of Mn salt concentration suppresses the oxidation loss of the lower aliphatic monocarboxylic acid used as the solvent.

As described above, in the oxidation process of tolualdehyde in the absence of the alkylbenzene, it is an essential condition for preventing the blackening of phthalic acid to maintain the Mn salt concentration at 40 ppm. or less in terms of Mn atoms in the reaction solution. On the other hand, in the case of adding 10% by weight of an alkylbenzene to tolualdehyde, the Mn salt concentration that causes no blackening of phthalic acid can be extended up to 170 ppm in terms of Mn atoms, in the case of the addition of 25% by weight of the alkylbenzene, it can be extended up to 320 ppm, and in the case of the addition of 50% by weight of the alkylbenzene, it can be extended up to 420 ppm.

In other words, the Mn salt concentration in the reaction solution can be extended in a range satisfying the following formula (1);

$$M \leq -0.15A^2 + 15A + 40 \quad (1)$$

where M is a Mn atom concentration (ppm by weight) on the basis of the reaction solution, and A is an amount (% by weight) of an alkylbenzene added on the basis of the total of tolualdehyde and said alkylbenzene, and is in a range of from more than 0 to 50 inclusive.

That is, the present invention provides a process for preventing a blackening of phthalic acid in the production of phthalic acid by oxidizing, in liquid phase, tolualdehyde with molecular oxygen or a gas containing the molecular oxygen in the presence of heavy metal salt containing a Mn salt, especially both Mn and Co salts, and a bromine compound, using a lower aliphatic monocarboxylic acid as a solvent, which comprises conducting the oxidation of tolualdehyde in the presence of an alkylbenzene in an amount satisfying the following formula (1);

$$M \leq -0.15A^2 + 15A + 40 \quad (1)$$

wherein M is a Mn atom concentration in ppm by weight on the basis of the reaction solution, and A is an amount in % by weight of the alkylbenzene added on the basis of the total of tolualdehyde and said alkylbenzene, and is in a range of from more than 0 to 50 inclusive.

As the tolualdehyde as the starting material for the present process, p-tolualdehyde is industrially most important on the ground of easy availability as well as of industrial value of the oxidation product.

Tolualdehyde of any origin can be used in the present invention. As to p-tolualdehyde, the one synthesized from toluene and carbon monoxide using hydrogen fluoride and boron trifluoride as a catalyst is used industrially, but the origin of p-tolualdehyde is not restricted.

As the alkylbenzene to be added to tolualdehyde, mono-, di-, or tri-alkyl-substituted benzene having lower alkyl groups such as methyl, ethyl and propyl groups can be used. These alkylbenzenes are oxidized to the corresponding aromatic carboxylic acids together with tolualdehyde. Thus, p-dialkylbenzenes that can be oxidized to terephthalic acid, particularly p-xylene, are useful.

In the present invention, it is preferable to use a Mn salt, Co salt and bromine compound as catalyst components. As the Mn salt and Co salt, any of their inorganic acid salts and organic acid salts can be used, but it is desirable to use compounds soluble in the solvent. It is preferable to use 100 to 5,000 ppm. of the Co salt in terms of Co atoms, based on the solvent. As to the amount of the Mn salt, it is necessary to use the Mn salt at a Mn concentration of at least 5 ppm in terms of Mn atoms, based on the reaction solution, to obtain the sufficient catalytic effect as described above. As the bromine compound, inorganic bromine salts such as ammonium salt, sodium salt and potassium salt, etc. or hydrogen bromide or organobromine compounds such as tetrabromoethane, tetrabromoparaxylene, etc. can be used. It is preferable to use 500 to 5,000 ppm of the bromine compound in terms of bromine atoms on the basis of the solvent.

Reaction temperature applicable to the practice of the present invention is in a range of from 120° C. to 240° C. Since the reaction is carried out in a liquid phase, it is usually necessary to apply a pressure to the reaction system to maintain tolualdehyde and the solvent in a liquid phase. A reaction pressure of 1 to 50 atm is used.

As the oxidizing agent, molecular oxygen or a gas containing the molecular oxygen is used, but it is economically advantageous to use air as the oxidizing agent.

As the lower aliphatic carboxylic acid used as the solvent, acetic acid, propionic acid, butyric acid, etc. can be used, but acetic acid is particularly preferable. It is satisfactory to use the solvent in an amount in weight at least twice the weight of tolualdehyde.

The present invention will be described in detail below, referring to Examples.

EXAMPLE 1

Into a titanium pressure-resistant reactor vessel (capacity: 500 ml) provided with a reflux condenser, a stirrer and a heater, and a feed inlet and a gas inlet were charged 0.790 g of cobalt acetate tetrahydrate, 0.159 g of manganese acetate tetrahydrate, 0.324 g of sodium bromide and 210 g of acetic acid in advance. Proportions of catalyst components to acetic acid were 890 ppm of Co, 170 ppm of Mn and 1,200 ppm of Br in terms of the respective atoms.

$N_2$ was charged at 10 kg/cm² gauge to the reactor vessel containing said catalyst and acetic acid, and then the reactor vessel was heated up to 205° C. by the heater. Then 80 g of a mixture of p-tolualdehyde and p-xylene (p-tolualdehyde:p-xylene=9:1 by weight) was continuously fed to a constant rate into the reactor vessel over a period of one hour at a temperature of 205° C. and a pressure of 20 kg/cm² gauge, while feeding air into the reactor vessel to carry out the reaction. Even after the end of feeding the raw material, air was fed thereto for further 5 minutes, and then the reactor vessel was cooled, and the content was taken out of the reactor vessel. In one hour, 72 g (0.599 moles) of p-tolualdehyde and 8 g (0.0753 moles) of p-xylene were fed as the raw materials.

The resulting product solution having slurry cooled to room temperature was filtered through a glass filter, and the resulting cakes were washed with acetic acid and then water, and dried at 110° C., whereby 108.2 g (0.651 moles) of terephthalic acid was obtained.

Properties and yield of the terephthalic acid thus obtained are given in Table 1.

EXAMPLE 2

Into the same reactor vessel used in Example 1 were charged the same amounts of coblat acetate tetrahydrate, sodium bromide and acetic acid as in Example 1, and 0.281 g of manganese acetate tetrahydrate (300 ppm in terms of Mn atoms on the basis of acetic acid) in advance. Then, 80 g of a mixture of p-tolualdehyde and p-xylene (p-tolualdehyde:p-xylene=3:1 by weight) was continuously fed at a constant rate to the reactor vessel over a period of one hour at a temperature of 205° C. and a pressure of 20 kg/cm² gauge while feeding air to the reactor vessel to carry out the reaction. In one hour, 60 g (0.500 moles) of p-tolualdehyde and 20 g (0.188 moles) of p-xylene were fed as the raw materials.

After the completion of the reaction, the resulting product was treated in the same way as in Example 1, whereby 111.2 g (0.669 moles) of terephthalic acid was obtained. Properties and yield of the terephthalic acid thus obtained are shown in Table 1.

EXAMPLE 3

Into the same reactor vessel as used in Example 1 were charged the same amounts of cobalt acetate tetrahydrate, sodium bromide and acetic acid as in Example 1, and 0.393 g of manganese acetate tetrahydrate (405 ppm in terms of Mn atoms on the basis of acetic acid) in advance. Then, 80 g of a mixture of p-tolualdehyde and p-xylene at a ratio of 1:1 by weight was continuously fed at a constant rate to the reactor vessel over a period of one hour at a temperature of 210° C. and a pressure of 20 kg/cm² gauge, while feeding air to the reactor vessel to carry out the reaction. In one hour 40 g (0.333 moles) of p-tolualdehyde and 40 g (0.377 moles) of p-xylene were fed as the raw materials.

After the completion of the reaction, the resulting product was treated in the same way as in Example 1, whereby 114.3 g (0.688 moles) of terephthalic acid was obtained. Properties and yield of the terephthalic acid thus obtained are shown in Table 1.

COMPARATIVE EXAMPLES 1-3

In Comparative Examples 1-3, p-tolualdehyde containing p-xylene was subjected to the reaction under the same conditions as the corresponding Examples 1-3, respectively, except that only the Mn salt concentrations of Examples 1-3 were made over the limit of Mn atom concentration in formula (1).

That is, a mixture of p-tolualdehyde and p-xylene (p-tolualdehyde:p-xylene=9:1 by weight) was oxidized in the presence of 0.187 g of manganese acetate tetrahydrate (Mn atom concentration:220 ppm) in Comparative Example 1, a mixture of p-tolualdehyde and p-xylene (p-tolualdehyde:p-xylene=3:1 by weight) in the presence of 0.375 g of manganese acetate tetrahydrate (Mn atom concentration:400 ppm) in Comparative Example 2, and a mixture of p-tolualdehyde and p-xylene (p-tolualdehyde:p-xylene=1:1 by weight) in the presence of 0.562 g of manganese acetate tetrahydrate (Mn atom concentration:600 ppm) in Comparative Example 3. The individual products were treated in the same way as in Example 1 to obtain terephthalic acid. Properties and yields of the individual terephthalic acids thus obtained are shown in Table 1.

Table 1

| | p-Xylene content in PTAL* (weight %) | Mn atom concentration on the basis of solvent (ppm) | Properties of terephthalic acid | | | | Terephthalic acid yield (mole %) |
|---|---|---|---|---|---|---|---|
| | | | Appearance | 4-CBA content (ppm) | Alkaline color | Ashes (ppm) | |
| Example 1 | 10 | 170 | White | 793 | 0.423 | 4.1 | 96.6 |
| Example 2 | 25 | 300 | White | 885 | 0.541 | 2.7 | 97.3 |
| Example 3 | 50 | 405 | White | 950 | 0.650 | 2.3 | 97.0 |
| Comparative Example 1 | 10 | 200 | Blackish brown | 826 | ∞ | 373 | 95.1 |
| Comparative Example 2 | 25 | 400 | Grey | 840 | ∞ | 57 | 96.9 |
| Comparative Example 3 | 50 | 600 | Grey | 950 | ∞ | 73 | 96.7 |

*PTAL = p-tolualdehyde

In Table 1, "alkaline color" is an optical density of a solution prepared by dissolving 2 g of a sample in 25 ml. of an aqueous 2 N KOH solution, with a light at 340 m$\mu$ in a 50 mm cell.

"Terephthalic acid yield" is a yield of terephthalic acid in moles on the basis of the total of p-tolualdehyde and p-xylene.

When the terephthalic acids obtained in Examples 1-3 were purified by hydrogenating them with molecular hydrogen in the presence of a catalyst and subsequent recrystallization according to Japanese Patent Publication No. 16860/66, the resulting purified terephthalic acids had such properties as white appearance, alkaline color of not more than 0.090 and 4-CBA content in 10 ppm or less. Polyethylene terephthalate obtained by reaction of said purified terephthalic acid with ethylene glycol was clear.

In contrast to the terephthalic acids obtained in Examples 1-3, the terephthalic acids obtained in Comparative Examples 1-3 were all colored, and no improvement in alkaline color was attained even by the hydrogenation-recrystallization treatment according to Japanese Patent Publication No. 16860/66. Polyethylene terephthalate obtained from the thus treated terephthalic acids of Comparative Examples 1-3 had an appearance of dary grey.

EXAMPLE 4

Into the same reactor vessel as used in Example 1 were charged 0.790 g of cobalt acetate tetrahydrate, 0.0937 g of manganese acetate tetrahydrate, 0.393 g of sodium bromide and 210 g of acetic acid in advance. Concentration of the catalyst components on the basis of acetic acid were 890 ppm of Co, 100 ppm of Mn, and 1200 ppm of Br. Then, 80 g of a mixture of p-tolualdehyde and p-xylene (p-tolualdehyde:p-xylene=3:1 by weight) was continuously fed at a constant rate to the reactor vessel over a period of one hour at a temperature of 205° C. and a pressure of 20 kg/cm² gauge, while feeding air into the reactor vessel to carry out oxidation. The resulting product was treated in the same way as in Example 1, whereby 110.1 g (0.663 moles) of terephthalic acid was obtained. Properties and yield of the terephthalic acid thus obtained are shown in Table 2.

EXAMPLE 5

Into the same reactor vessel as used in Example 1 were charged the same amounts of cobalt acetate tetrahydrate, sodium bromide and acetic acid as in Example 4 in advance, except that 0.187 g of manganese acetate tetrahydrate was used. Concentrations of the catalytic components on the basis of acetic acid were 890 ppm of Co, 200 ppm of Mn and 1200 ppm of Br. Then 80 g of a mixture of p-tolualdehyde and p-xylene (p-tolualdehyde:p-xylene=3:1 by weight) was oxidized with air under the same reaction conditions and in the same way as in Example 4, whereby 110.9 g (0.667 moles) of terephthalic acid was obtained. Properties and yield of the terephthalic acid thus obtained are shown in Table 2.

of acetic acid in advance. Concentrations of catalyst components on the basis of acetic acid were 890 ppm of Co, 170 ppm of Mn, and 1200 ppm of Br. Then, 80 g of a mixture of p-tolualdehyde and toluene (p-tolualdehyde:toluene=9:1 by weight) was continuously fed at a constant rate to the reactor vessel over a period of one hour at a temperature of 205° C. and a pressure of 20 kg/cn² gauge, while feeding air to the reactor vessel to carry out the oxidation. The resulting product was treated in the same way as in Example 1, whereby 95.9 g (0.577 moles) of terephthalic acid was obtained. Properties and yield of the terephthalic acid thus obtained are given as follows:

| Appearance: | white |
|---|---|
| Alkaline color: | 0.443 |
| 4-CBA content: | 812 ppm |
| Ashes: | 3.9 ppm |
| Terephthalic acid yield: | 96.4% by mole |

What is claimed is:

1. In a process for producing phthalic acid by the oxidation, in a liquid phase, of tolualdehyde with molecular oxygen or a gas containing molecular oxygen in the presence of an Mn salt and bromine employing a lower aliphatic monocarboxylic acid as a solvent, the im- Table 2

| | Mn atom concentration on the basis of acetic acid (ppm) | Properties of terephthalic acid | | | | Terephthalic acid yield (mole %) |
|---|---|---|---|---|---|---|
| | | Appearance | 4-CBA content (ppm) | Alkaline color | Ashes (ppm) | |
| Example 4 | 100 | White | 790 | 0.467 | 2.5 | 96.3 |
| Example 5 | 200 | White | 813 | 0.482 | 3.0 | 37.0 |

EXAMPLE 6

In the same reactor vessel as used in Example 1 were charged 1.775 g of cobalt acetate tetrahydrate, 0.281 g of manganese acetate tetrahydrate, 0.733 g of sodium bromide and 210 g of acetic acid in advance. Concentrations of catalyst components were 2000 ppm of Co, 300 ppm of Mn and 2710 ppm of Br, on the basis of acetic acid. Then, 60 g of a mixture of p-tolualdehyde and p-xylene (p-tolualdehyde:p-xylene=3:1 by weight) was continuously fed at a constant rate to the reactor vessel over a period of 2 hours at a temperature of 200° C. and a pressure of 20 kg/cm² gauge, while feeding air to the reactor vessel to carry out oxidation. In two hours, 45 g (0.375 moles) of p-tolualdehyde and 15 g (0.141 moles) of p-xylene were fed as the raw materials.

The resulting product was treated in the same way as in Example 1, whereby 81.4 g (0.490 moles) of terephthalic acid was obtained. Properties and yield of the terephthalic acid thus obtained are given as follows:

| Appearance: | white |
|---|---|
| Alkaline color: | 0.130 |
| 4-CBA content: | 360 ppm |
| Ashes: | 3.0 ppm |
| Terephthalic yield: | 95.0 mole % |

EXAMPLE 7

Into the same reactor vessel as used in Example 1 were charged 0.790 g of cobalt acetate tetrahydrate, 0.159 g of manganese acetate tetrahydrate, 0.510 g of hydrogen bromide (in aqueous 50% solution), and 210 g provement comprising conducting the oxidation of the tolualdehyde in the presence of an alkylbenzene in an amount satisfying the formula $$M \leq -0.15 A^2 + 15 A + 40$$

wherein M is the Mn atom concentration in ppm by weight on the basis of the reaction solution, said reaction solution being the total of solvent and water present in the reaction system, and A is an amount in % by weight of the alkylbenzene added based on the total amount of the tolualdehyde and the alkylbenzene and is in a range of from more than 0 to 50 inclusive.

2. A process according to claim 1, wherein the tolualdehyde is p-tolualdehyde.

3. A process according to claim 1, wherein the tolualdehyde is p-tolualdehyde and alkylbenzene is p-xylene.

4. A process according to claim 1, wherein the Mn atom concentration is at least 5 ppm.

5. A process according to claim 1, wherein the oxidation is carried out at a reaction temperature of from 120° to 240° C. and a pressure of 1 to 50 atm.

6. In a process for producing phthalic acid by the oxidation, in a liquid phase, of tolualdehyde with molecular oxygen or a gas containing molecular oxygen in the presence of an Mn and a Co salt and bromine employing a lower aliphatic monocarboxylic acid as a solvent, the improvement comprising conducting the oxidation of the tolualdehyde in the presence of an alkylbenzene in an amount satisfying the formula $$M \leq -0.15 A^2 + 15A + 40$$

wherein M is the Mn atom concentration in ppm by weight on the basis of the reaction solution, said reaction solution being the total of solvent and water present in the reaction system, and A is an amount in % by weight of the alkylbenzene added based on the total amount of the tolualdehyde and the alkylbenzene and is in a range of from more than 0 to 50 inclusive.

7. A process according to claim 6, wherein the tolualdehyde is p-tolualdehyde.

8. A process according to claim 6, wherein the tolualdehyde is p-tolualdehyde and alkylbenzene is p-xylene.

9. A process according to claim 6, wherein the Mn atom concentration is at least 5 ppm.

10. A process according to claim 6, wherein the oxidation is carried out at a reaction temperature of from 120° to 240° C. and a pressure of 1 to 50 atm.

11. A process according to claim 6, wherein the Co atom concentration is in a range of 100–5000 ppm by weight based on the solvent.

* * * * *